US012412657B2

(12) United States Patent
Muse et al.

(10) Patent No.: US 12,412,657 B2
(45) Date of Patent: Sep. 9, 2025

(54) ARTIFICIAL HEART CONTROL SYSTEMS AND METHODS

(71) Applicant: UnitedHealth Group Incorporated, Minnetonka, MN (US)

(72) Inventors: Jon Kevin Muse, Thompsons Station, TN (US); Gregory J. Boss, Saginaw, MI (US); Komal Khatri, Cedar Park, TX (US); Marilyn L. Gordon, Cherry Hill, NJ (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 885 days.

(21) Appl. No.: 17/466,681

(22) Filed: Sep. 3, 2021

(65) Prior Publication Data

US 2023/0076293 A1 Mar. 9, 2023

(51) Int. Cl.
*G16H 40/60* (2018.01)
*A61M 60/196* (2021.01)
(Continued)

(52) U.S. Cl.
CPC .......... *G16H 40/63* (2018.01); *A61M 60/196* (2021.01); *A61M 60/531* (2021.01); *A61M 60/892* (2021.01); *G06F 9/54* (2013.01); *G16H 20/40* (2018.01); *G16H 40/60* (2018.01); *A61M 2205/3523* (2013.01); *A61M 2205/52* (2013.01)

(58) Field of Classification Search
CPC ..... G16H 40/60; G16H 40/63; A61M 60/196; A61M 60/531; A61M 2205/3523; A61M 2205/52; G06F 9/54
See application file for complete search history.

(56) References Cited

U.S. PATENT DOCUMENTS 4,213,207 A 7/1980 Wilson
6,183,412 B1 2/2001 Benkowski et al.
(Continued)

OTHER PUBLICATIONS

"7 Things You Should Know About Artificial Hearts," SynCardia, (8 pages), [article, online], [Retrieved from the Internet Sep. 7, 2021] <https://syncardia.com/patients/media/blog/2018/08/seven-things-about-artificial-hearts/>.
(Continued)

*Primary Examiner* — Dinah Baria
(74) *Attorney, Agent, or Firm* — Alston & Bird LLP

(57) ABSTRACT

A controller for an artificial heart enables activity-specific adjustments to the operation of an artificial heart by obtaining sensor data from a plurality of sensors monitoring characteristics of a patient's body, and using the sensor data as input to one or more control parameter models for identifying control parameters to be provided to the artificial heart to adjust the operational parameters of the artificial heart. The controller is in wireless communication with the artificial heart via an application program interface (API)-based communication channel that facilitates communication between the controller and the artificial heart. Moreover, a cloud-based management computing entity may be utilized to train and/or execute one or more models to enable real-time updates to the operational characteristics of the artificial heart to enable the artificial heart to appropriately accommodate activities of the patient.

9 Claims, 6 Drawing Sheets

(51) Int. Cl.
*A61M 60/531* (2021.01)
*A61M 60/892* (2021.01)
*G06F 9/54* (2006.01)
*G16H 20/40* (2018.01)
*G16H 40/63* (2018.01)

(56) References Cited

U.S. PATENT DOCUMENTS

| | | | |
|---|---|---|---|
| 9,089,633 | B2 | 7/2015 | Ogawa et al. |
| 9,861,729 | B2 | 1/2018 | Morello et al. |
| 10,660,998 | B2 | 5/2020 | Hodges |
| 2010/0222633 | A1 | 9/2010 | Poirier |
| 2017/0312072 | A1 | 11/2017 | Grandy |
| 2019/0184081 | A1* | 6/2019 | Shu .............. A61M 60/268 |

OTHER PUBLICATIONS

"Target Heart Rates Chart," American Heart Association, Mar. 9, 2021, (4 pages), [article, online], https://www.heart.org/en/healthy-living/fitness/fitness-basics/target-heart-rates.

"What's Next for Pediatric-Scaled Continuous-Flow Total Artificial Heart," Cleveland Clinic, Consult QD, (4 pages), Dec. 4, 2019, [article, online], [Retrieved from the Internet Sep. 7, 2021] <https://consultqd.clevelandclinic.org/whats-next-for-pediatric-scaled-continuous-flow-total-artificial-heart/>.

Bailey, Stephanie. "This New Artificial Heart Responds to the Patient," CNN Business, (5 pages), Mar. 25, 2021, [article, online], [Retrieved from the Internet Sep. 7, 2021] <https://www.cnn.com/2021/03/25/business/carmat-artificial-heart-spc-intl/index.html>.

Mullin, Emily. "A Simple Artificial Heart Could Permanently Replace a Failing Human One," MIT Technology Review, Mar. 16, 2018, (9 pages), [article, online], [Retrieved from the Internet Sep. 7, 2021] <https://www.technologyreview.com/2018/03/16/104612/a-simple-artificial-heart-could-permanently-replace-a-failing-human-one/>.

Nicholson, Clare et al. "Total Artificial Heart and Physical Therapy Management," Cardiopulmonary Physical Therapy Journal, vol. 21, No. 2, pp. 13-21, Jun. 2010, DOI: ncbi.nlm.nih.gov/pmc/articles/PMC2879422/pdf/cptj0021-0013.pdf, PMCID: PMC2879422, PMID: 20520759.

Roland, James. "How to Get a Great Workout With Brisk Walking," Healthline, Dec. 9, 2019, (12 pages), [article, online], [Retrieved from the Internet Sep. 7, 2021] <https://www.healthline.com/health/brisk-walking#target-heart-rate>.

Segers, Patrick et al. "How to Measure Arterial Stiffness in Humans," Arteriosclerosis, Thrombosis, and Vascular Biology, May 2020, vol. 40, pp. 1034-1043, DOI: 10.1161/ATVBAHA.119.313132.

Wang, Yu et al. "Sensor-Based Physiologic Control Strategy for Biventricular Support with Rotary Blood Pumps," Asaio Journal, Jun. 2018, vol. 64, Issue 3, pp. 338-350, DOI: 10.1097/MAT.0000000000000671.

Requirement for Restriction/Election Mailed on Sep. 18, 2024 for U.S. Appl. No. 17/466,728, 6 page(s).

Non-Final Rejection Mailed on Feb. 25, 2025 for U.S. Appl. No. 17/466,728, 9 page(s).

* cited by examiner

ARTIFICIAL HEART CONTROL SYSTEMS AND METHODS

BACKGROUND

Artificial hearts provided to patients are very limited in functionality. Artificial hearts are generally provided on a temporary basis, such as while a patient awaits a heart transplant. Patients are very limited in their activities while using an artificial heart, as the artificial hearts are generally incapable of dynamically adjusting flowrate to match a bodily function and/or patient activity.

The constant or near constant functionality of artificial hearts can also result in relatively fast wear and tear on the mechanical components of the artificial heart, thereby ensuring a generally limited lifespan of the artificial heart.

Thus, a need exists for systems and methods for providing precise control of artificial heart functionality to more closely match a patient's bodily functions during normal patient activities.

BRIEF SUMMARY

Described herein are controllers and corresponding methods of using the controllers for adjusting the functionality of an artificial heart functioning with a patient's body to more appropriately match the patient's body function during normal patient activities. The controller is configured to receive signals from a plurality of sensors monitoring various aspects of the patient's body and for generating appropriate control parameter data for the artificial heart to appropriately match the patient's body function based at least in part on the signals received from the various sensors. Artificial heart control based at least in part on the received sensor signals may be determined via one or more machine-learning based models for determining appropriate flowrates for the artificial heart upon receipt of various sensor signal levels and/or based at least in part on care provider (e.g., physician) input. The control parameter data is provided from the controller to the artificial heart via an application program interface (API)-based communication protocol, thereby enabling the controller to function with multiple artificial heart types.

Certain embodiments are directed to a method for controlling an artificial heart, the method comprising: receiving patient-specific acceptable operational parameter data defining acceptable operational parameters for the artificial heart, wherein the patient-specific acceptable operational parameter data is generated based at least in part on user input provided for a patient; receiving sensor data generated by one or more body sensors each monitoring characteristics of the patient's body, wherein the sensor data comprises data identifying current operational parameters of the artificial heart; determining a body state for the patient's body based at least in part on the sensor data; identifying, based at least in part on the body state, one or more applicable acceptable operational parameters selected from the patent-specific acceptable operational parameter data for application to the artificial heart; determining control parameters to be applied to the artificial heart that satisfy the one or more acceptable operational parameters; determining, via a ramp model and based at least in part on the control parameters, a ramp rate for implementing the control parameters by the artificial heart; and causing the control parameters to be wirelessly transmit to the artificial heart via an application program interface (API)-based communication channel to cause the artificial heart to adjust current operational parameters to reflect the control parameters according to the ramp rate in real-time.

In various embodiments, the method further comprises receiving updated patient-specific acceptable operational parameter data generated based at least in part on updated user input provided for the patient, and wherein determining control parameters to be applied to the artificial heart comprises determining control parameters that satisfy the updated patient-specific acceptable operational parameter data. In certain embodiments, the method further comprises monitoring the API-based communication channel for one or more trigger conditions, and upon detecting a trigger condition, causing the artificial heart to operate in a safety mode at a constant blood flow rate. In various embodiments, receiving sensor data comprises receiving one or more of: blood pressure data, blood oxygenation data, body temperature data, or blood glucose level data. In certain embodiments, receiving sensor data comprises receiving sensor data generated by the artificial heart and transmitted via the API-based communication channel. In certain embodiments, receiving sensor data comprises receiving sensor data generated by one or more sensors attached to the patient's body. In various embodiments, the method further comprises: receiving data indicative of user input requesting a heart rate boost; and causing data indicative of the requested heart rate boost to be transmitted to the artificial heart via the API-based communication channel to cause the artificial heart to adjust the operational parameters to satisfy the requested heart rate boost.

Certain embodiments are directed to a controller for an artificial heart, wherein the controller comprises one or more memory storage areas, one or more processors, and a communication interface for wirelessly communicating with the artificial heart, wherein the controller is configured to: receive sensor data generated by one or more body sensors each monitoring characteristics of a patient's body, wherein the sensor data comprises data identifying current operational parameters of the artificial heart; determine a body state for the patient's body based at least in part on the sensor data; identify, based at least in part on the body state, one or more acceptable operational parameters for application to the artificial heart, wherein the one or more acceptable operational parameters are stored in a memory storage area together with a body state tag and wherein the one or more acceptable operational parameters reflect user input provided to a user computing entity establishing acceptable operational parameters for one or more body states for the patient; determine, based at least in part on a control parameter model, control parameters to be applied to the artificial heart that satisfy the one or more acceptable operational parameters; determine, based at least in part on a ramp model and based at least in part on the control parameters and current operational parameters, a ramp rate for implementing the control parameters by the artificial heart; and wirelessly transmit the control parameters and data reflecting the ramp rate to the artificial heart via an application program interface (API)-based communication channel to cause the artificial heart to adjust the current operational parameters to reflect the control parameters according to the ramp rate in real-time.

In certain embodiments, the controller is configured to receive the sensor data via a wireless communication channel between the controller and one or more sensors attached to the patient's body. In various embodiments, the controller is configured to receive the sensor data via the API-based communication channel from the artificial heart. In certain embodiments, the sensor data comprises one or more of: blood pressure data, blood oxygenation data, body temperature data, or blood glucose level data. Moreover, in various embodiments, the controller is in communication with a management computing entity, and wherein: determining control parameters to be applied to the artificial heart comprises transmitting at least a portion of the sensor data to the management computing entity for execution of the control parameter model; and determining a ramp rate comprises transmitting at least a portion of the sensor data to the management computing entity for execution of the ramp model.

In various embodiments, the controller is further configured to monitor the API-based communication channel for one or more trigger conditions, and upon detecting a trigger condition, causing the artificial heart to operate in a safety mode at a constant blood flow rate.

Certain embodiments are directed to an artificial heart system comprising: an artificial heart for circulating blood within a patient's body, the artificial heart comprising a wireless communication interface; a controller comprising one or more memory storage areas, one or more processors, and a wireless communication interface configured to establish a wireless communication channel with the artificial heart for data exchange via an application program interface (API)-based communication protocol, wherein the controller is configured to: receive sensor data generated by one or more body sensors each monitoring characteristics of a patient's body, wherein the sensor data comprises data identifying current operational parameters of the artificial heart; determine a body state for the patient's body based at least in part on the sensor data; identify, based at least in part on the body state, one or more acceptable operational parameters for application to the artificial heart, wherein the one or more acceptable operational parameters are stored in a memory storage area together with a body state tag and wherein the one or more acceptable operational parameters reflect user input provided to a user computing entity establishing acceptable operational parameters for one or more body states for the patient; determine, based at least in part on a control parameter model, control parameters to be applied to the artificial heart that satisfy the one or more acceptable operational parameters; determine, based at least in part on a ramp model and based at least in part on the control parameters and current operational parameters, a ramp rate for implementing the control parameters by the artificial heart; and wirelessly transmit the control parameters and data reflecting the ramp rate to the artificial heart via an application program interface (API)-based communication channel to cause the artificial heart to adjust the current operational parameters to reflect the control parameters according to the ramp rate in real-time.

In various embodiments, the controller is configured to receive the sensor data via a wireless communication channel between the controller and one or more sensors attached to the patient's body. In certain embodiments, the controller is configured to receive the sensor data via the API-based communication channel from the artificial heart. In various embodiments, the sensor data comprises one or more of: blood pressure data, blood oxygenation data, body temperature data, or blood glucose level data. In certain embodiments, the artificial heart system further comprises a management computing entity in networked communication with the controller, and wherein: determining control parameters to be applied to the artificial heart comprises transmitting at least a portion of the sensor data to the management computing entity for execution of the control parameter model; and determining a ramp rate comprises transmitting at least a portion of the sensor data to the management computing entity for execution of the ramp model.

In certain embodiments, the controller is further configured to monitor the API-based communication channel for one or more trigger conditions, and upon detecting a trigger condition, causing the artificial heart to operate in a safety mode at a constant blood flow rate.

Various embodiments are directed to a method for controlling an artificial heart, the method comprising: receiving, at an artificial heart and via a wireless, application program interface (API)-based communication channel, control parameter data from a controller, wherein the control parameter data is configured to adjust implemented operational parameters of the artificial heart based at least in part on sensor data generated from one or more sensors monitoring characteristics of a patient's body; implementing the control parameter data by adjusting the operational parameters of the artificial heart based at least in part on the control parameter data; monitoring one or more of: operation of hardware of the artificial heart and communications received via the API-based communication channel to detect a trigger condition; and upon detecting a trigger condition, implementing safe mode parameters stored within a local memory storage area of the artificial heart by adjusting the operational parameters based at least in part on the safe mode parameters, wherein the safe mode parameters identify a constant flow rate of blood for implementation by the artificial heart.

In certain embodiments, detecting a trigger condition comprises receiving trigger condition data from the controller via the API-based communication channel. In various embodiments, the trigger condition comprises data indicating a low blood pressure measurement of the patient's body. Moreover, detecting a trigger condition may comprise determining that the API-based communication channel has been disconnected.

In certain embodiments, detecting a trigger condition comprises detecting one or more hardware malfunctions of hardware components of the artificial heart. In various embodiments, detecting a trigger condition comprises determining that the API-based communication channel has been compromised. In certain embodiments, the method further comprises: monitoring one or more of: operation of hardware of the artificial heart and communications received via the API-based communication channel to detect remediation of the trigger condition; and upon determining that the trigger condition has been remedied: receiving updated control parameter data from the controller; and implementing the updated control parameter data by modifying the operational parameters based at least in part on the updated control parameter data. In certain embodiments, detecting remediation of the trigger condition comprises receiving data from the controller indicative of user input identifying the trigger condition as being remedied.

Various embodiments are directed to an artificial heart comprising one or more pumps and one or more valves for controlling blood flow within a patient and comprising one or more memory storage areas and one or more processors collectively configured to control the operation of the one or more pumps and one or more valves, wherein the one or more memory storage areas and one or more processors are collectively configured to: receive, via a wireless, application program interface (API)-based communication channel, control parameter data from a controller, wherein the control parameter data is configured to adjust implemented operational parameters of the artificial heart based at least in part on sensor data generated from one or more sensors monitoring characteristics of a patient's body; implement the control parameter data by adjusting the operational parameters of the artificial heart based at least in part on the control parameter data to control operation of the one or more pumps and one or more valves; monitor one or more of: operation of hardware of the artificial heart and communications received via the API-based communication channel to detect a trigger condition; and upon detecting a trigger condition, implement safe mode parameters stored within a local memory storage area of the artificial heart by adjusting the operational parameters based at least in part on the safe mode parameters, wherein the safe mode parameters identify a constant flow rate of blood for implementation by the artificial heart.

In certain embodiments, detecting a trigger condition comprises receiving trigger condition data from the controller via the API-based communication channel. In various embodiments, the trigger condition comprises data indicating a low blood pressure measurement of the patient's body. In certain embodiments, detecting a trigger condition comprises determining that the API-based communication channel has been disconnected. In various embodiments, detecting a trigger condition comprises detecting one or more hardware malfunctions of hardware components of the artificial heart.

According to certain embodiments, detecting a trigger condition comprises determining that the API-based communication channel has been compromised. In various embodiments, the one or more memory storage areas and one or more processors of the artificial heart system are additionally configured to: monitor one or more of: operation of hardware of the artificial heart and communications received via the API-based communication channel to detect remediation of the trigger condition; and upon determining that the trigger condition has been remedied: receive updated control parameter data from the controller; and implement the updated control parameter data by modifying the operational parameters based at least in part on the updated control parameter data. In various embodiments, detecting remediation of the trigger condition comprises receiving data from the controller indicative of user input identifying the trigger condition as being remedied.

Certain embodiments are directed to a controller for an artificial heart, wherein the controller comprises one or more memory storage areas and one or more processors collectively configured to: transmit, via a wireless application program interface (API)-based communication channel, control parameter data to an artificial heart, wherein the control parameter data is configured to adjust implemented operational parameters of the artificial heart based at least in part on sensor data generated from one or more sensors monitoring characteristics of a patient's body; monitor one or more of: sensor data received from one or more body sensors sensing characteristics of the patient's body, sensor data received via the API-based communication channel from the artificial heart, or data received from a remote management computing entity to detect a trigger condition; upon detecting a trigger condition, transmit control parameter data reflecting safe mode parameters to the artificial heart to cause the artificial heart to adjust implemented operational parameters based at least in part on the safe mode parameters, wherein the control parameters reflecting the safe mode parameters identify a constant flow rate of blood for implementation by the artificial heart.

In certain embodiments, the trigger condition is identified based at least in part on sensor data indicating a blood pressure below a threshold value. In various embodiments, the trigger condition is identified based at least in part on a determination that the API-based communication channel has been compromised. According to certain embodiments, the one or more memory storage areas and one or more processors are additionally configured to: monitor one or more of: sensor data received from one or more body sensors sensing characteristics of the patient's body, sensor data received via the API-based communication channel from the artificial heart, or data received from a remote management computing entity to detect remediation of the trigger condition; and upon determining that the trigger condition has been remedied: transmit updated control parameter data to the artificial heart, wherein the updated control parameter data is reflective of updated sensor data received from the one or more body sensors to cause the artificial heart to implement the updated control parameter data by modifying the operational parameters based at least in part on the updated control parameter data.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

Figure 1:
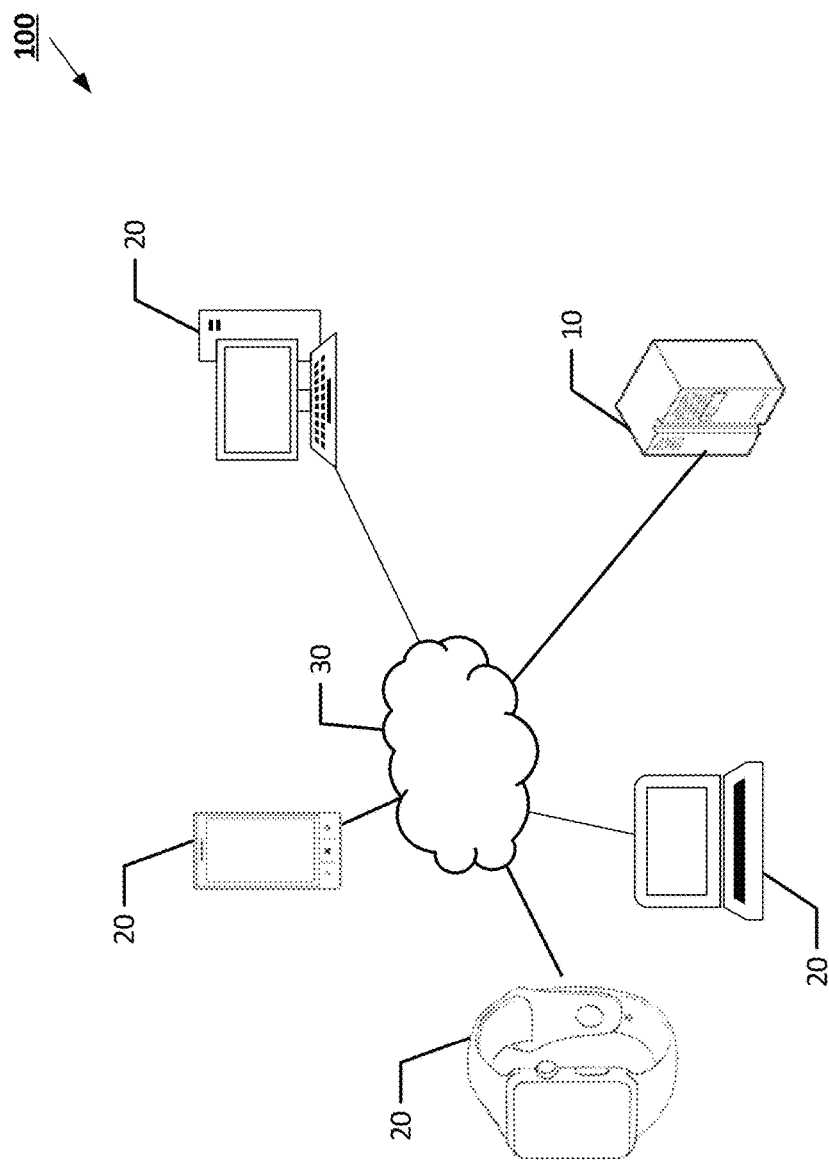
FIG. 1 is an exemplary overview of a system architecture that can be used to practice various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Overview

To enable artificial hearts to operate in a manner that more closely emulates the operation of a natural heart, various embodiments utilize an external controller (e.g., a mobile user computing entity or an executable software application operating on a mobile user computing entity) that is in wireless communication with the artificial heart hardware and which provides control parameters to control the operational parameters of the artificial heart based at least in part on sensor data received from a plurality of body sensors monitoring activities and/or characteristics of the patient's body. Collectively, the artificial heart and the controller (and a remote management computing entity, in certain embodiments) constitute an artificial heart system as discussed herein.

The controller, together with a remote management computing entity in certain implementations, intakes the received sensor data and uses the sensor data as input to one or more models (e.g., machine-learning models) to determine a current state of the patient (e.g., exercising, resting, sleeping, digesting) and to determine an appropriate flow rate for the artificial heart based at least in part on the determined patient body state and assigned flow rates for the patient (e.g., from within a plurality of acceptable operational parameters as assigned by the patient's physician). The controller then transmits control parameters to the artificial heart to adjust the operational parameters of the artificial heart (e.g., the flow rate).

The controller is additionally configured to implement a safe mode with the artificial heart (or the artificial heart may implement the safe mode via local operation, without input from the controller) upon the occurrence of one or more trigger conditions that may indicate a malfunction of the controller, a malfunction of the artificial heart, interference of the controller, and/or another trigger condition that suggests that the operation of the artificial heart should not, or cannot, be controlled by the controller. The safe mode may cause the artificial heart to operate at a continuous, preset flow rate established within the safe mode parameters (unaffected by sensor data) to maintain a life-sustaining level of blood flow within the patient until the trigger condition status may be rectified.

Technical Problem

Artificial hearts are generally operated to maintain a life-sustaining level of blood flow within the patient, and artificial hearts are generally provided to patients on a temporary basis, until a natural heart replacement becomes available to the patient. Partially because artificial hearts utilize external pump driving systems for operation of the artificial hearts, artificial hearts are incapable of responding to changes in the patient's body function due to changes in the patient's activities. For example, as the patient exercises, a healthy natural heart will gradually increase its pump rate to supply additional blood and oxygen throughout the body. However, a traditional artificial heart is incapable of receiving any signals from the body that are indicative of the patient's beginning of an period of exercise, and therefore the artificial heart pump rate remains constant (which generally impedes the patient's ability to exercise vigorously).

Technical Solution

To provide a more natural function of artificial hearts, an external controller (which may be embodied as a mobile user computing entity or other computing entity in wireless communication with the artificial heart) receives and processes signals from a plurality of sensors measuring various characteristics of the human body, and uses those sensor signals as input to one or more models (e.g., machine-learning models) to identify the appropriate heart rate for an artificial heart and the appropriate ramp rate (effectively, the appropriate rate of change of the heart rate) for adjusting heart rate (or other operational parameters) of the artificial heart so as to better emulate the functionality of a natural heart. Based at least in part on the output of the models, the controller transmits control parameters to the artificial heart to cause the artificial heart to adjust the operational parameters of the artificial heart to better match the patient's current body function.

Computer Program Products, Methods, and Computing Devices

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all non-transitory computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like). A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Exemplary System Architecture

FIG. 1 provides an example system architecture 100 that can be used in conjunction with various embodiments of the present invention. As shown in FIG. 1, the system architecture 100 may comprise one or more management computing entities 10, one or more user computing entities 20, one or more networks 30, and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

Exemplary Management Computing Entity

Figure 2:
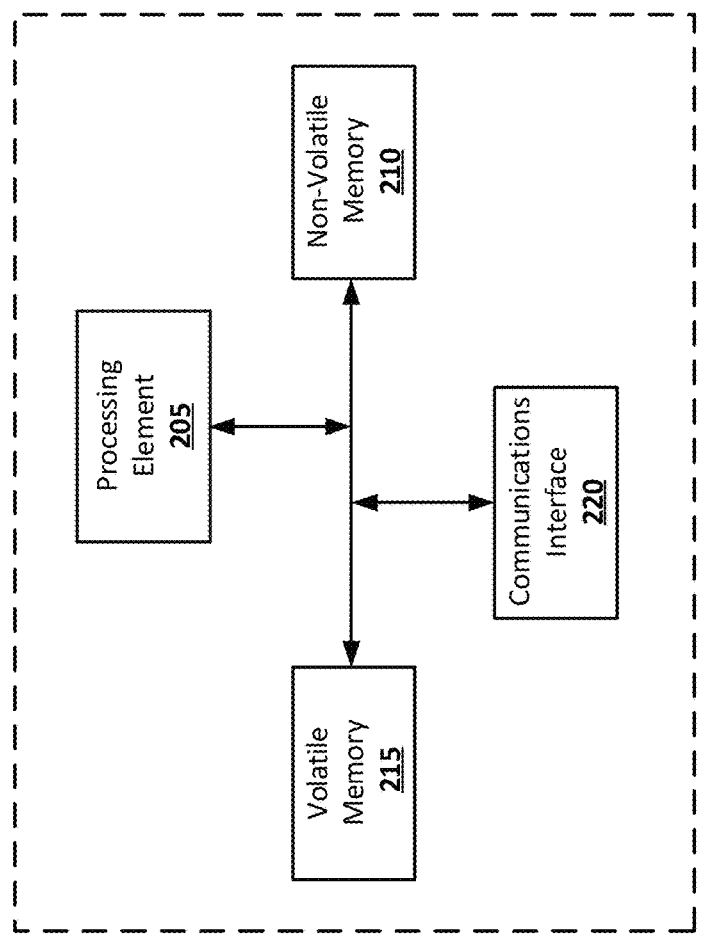
FIG. 2 is an example schematic of a management computing entity in accordance with certain embodiments.

FIG. 2 provides a schematic of a management computing entity 10 according to one embodiment of the present invention. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the management computing entity 10 may include or be in communication with one or more processing elements 205 (also referred to as processors, processing circuitry, and/or similar terms used herein interchangeably) that communicate with other elements within the management computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the management computing entity 10 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the management computing entity 10 may further include or be in communication with volatile media (also referred to as volatile storage, memory, memory storage, memory circuitry and/or similar terms used herein interchangeably). In one embodiment, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the management computing entity 10 with the assistance of the processing element 205 and the operating system.

As indicated, in one embodiment, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, management computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The management computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the management computing entity's components may be located remotely from other management computing entity 10 components, such as in a distributed system. Furthermore, one or more of the components may be aggregated and additional components performing functions described herein may be included in the management computing entity 10. Thus, the management computing entity 10 can be adapted to accommodate a variety of needs and circumstances, such as including various components described with regard to a mobile application executing on the user computing entity 20, including various input/output interfaces.

Exemplary User Computing Entity

Figure 3:
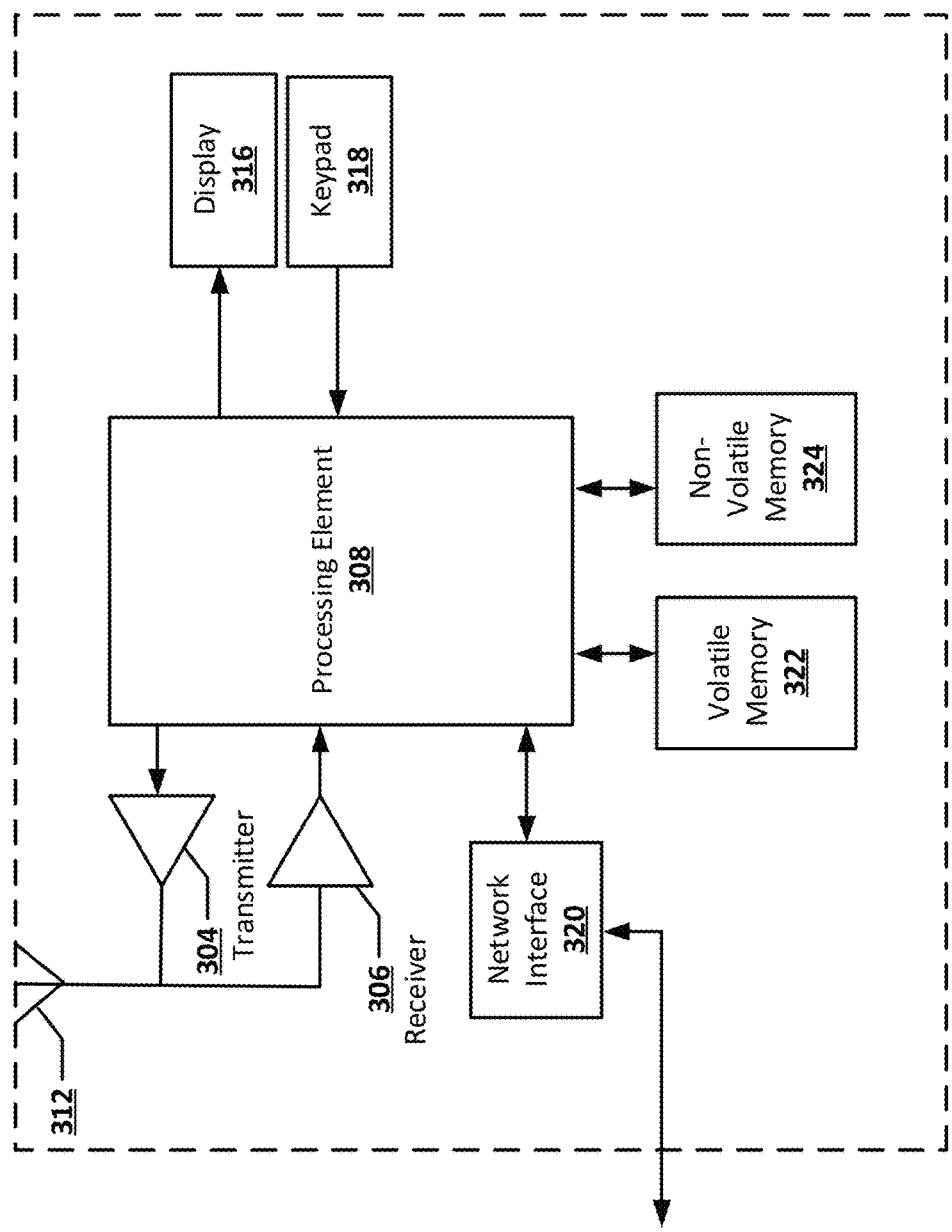
FIG. 3 is an example schematic of a user computing entity in accordance with certain embodiments.

FIG. 3 provides an illustrative schematic representative of user computing entity 20 that can be used in conjunction with embodiments of the present invention. In various embodiments, the user computing entity 20 may be or comprise one or more mobile devices, wearable computing devices, and/or the like. The user computing entity 20 may be utilized as a controller for an artificial heart or the user computing entity 20 may store a software-based application thereon that operates as a controller for the artificial heart. Thus, as just one example, a patient's user computing entity 20 (e.g., a smartphone) may provide the functionality of a controller as discussed herein.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a management computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any of a number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to one embodiment, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In one embodiment, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

Exemplary Networks

In one embodiment, any two or more of the illustrative components of the system architecture 100 of FIG. 1 may be configured to communicate with one another via one or more networks 30. The networks 30 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 30 may have any suitable communication range associated therewith and may include, for example, global networks (e.g., the Internet), MANs, WANs, LANs, or PANs. In addition, the networks 30 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

Example Artificial Heart

An example artificial heart is a pump that is surgically installed within a patient to provide circulation within the patient's body and to replace heart ventricles (e.g., generally to replace diseased or damaged heart ventricles). The artificial, installed pump circulates blood into and out of the lungs and other parts of the body. Example artificial hearts may be placed entirely within the patient's body (under the patient's skin). In other embodiments, portions of the artificial heart are implanted within the patient's body (under the patient's skin) and other portions are located external to the patient's body. Portions of the artificial heart that are internal to the human body and portions that are external to the human body may be in physical connection, such as via one or more wires, tubes, and/or the like passing through the patient's skin. In other embodiments, portions of the artificial heart that are internal to the human body and portions that are external to the human body may be in wireless communication, such as a controller located external to the human body that transmits control parameter data to the portion of the artificial heart located within the human body.

As just one example artificial heart, one or more pumps that define a portion of the hardware of the artificial heart are surgically installed within the patient's body to replace the lower ventricles of the patient's heart. The one or more pumps may comprise four mechanical valves (although more or fewer mechanical valves are provided in certain embodiments) within a total replacement artificial heart. The mechanical valves are configured to emulate a natural heart's valves for controlling blood flow. These valves connect the artificial heart to the remaining upper chambers of the patient's natural heart (the atrium) and to the major arteries, the pulmonary artery, and the aorta of the patient's body. The pumps may be pneumatically-controlled pumps, each having a connected pneumatic tube that passes through the patient's skin to an external, powered console that provides compressed air to the pumps to operate the pumps as needed. The powered console may additionally house one or more memory storage areas (e.g., storing firmware and/or storing safe mode operational parameters, as discussed herein), one or more processors, and/or one or more communication interfaces, as discussed herein. The pumps provide mechanical circulation of blood to restore at least substantially normal blood flow through the patient's body in accordance with implemented operational parameters (that may be modified/adjusted in response to control parameters received at the console, such as from the controller). The pneumatic, powered console may be controlled in accordance with control parameter data received from a separate controller, such as control parameter data received wirelessly from the separate controller.

The artificial heart itself may include an onboard control mechanism (e.g., as mentioned above in reference to the processing functionality housed within the console) comprising one or more memory storage areas, one or more processors, and a communication interface (the onboard control mechanism may have a configuration analogous to a user computing entity 20 discussed above). The onboard control mechanism is provided for self-monitoring the operation of the artificial heart, such as to ensure the current operational parameters are implemented, and the hardware is operating to maintain the current operational parameters within applicable and desired ranges (e.g., as established based at least in part on control parameters provided by the controller). Moreover, the onboard control mechanism monitors for malfunctions of the artificial heart (e.g., hardware malfunctions, malfunctions of the communication interface, and/or the like), so as to self-determine whether a safe-mode should be implemented. As discussed herein, the one or more memory storage areas store operational parameter data corresponding to the safe-mode, such that the artificial heart is capable of operating without communication with separate computing entities (e.g., the controller), if needed. The onboard control mechanism encompasses the communication interface for communicating (e.g., wirelessly, via short-range wireless communication channels) with the controller (e.g., via an API-based communication protocol) for receiving control parameters and for transmitting data (e.g., sensor data) indicative of the current operation of the artificial heart.

Example Body Sensors

The controller is configured to receive signals from a plurality of body sensors monitoring various characteristics of the patient's body. Those body sensors may be physically and/or electrically connected with the controller and/or the artificial heart. Others of those sensors are in wireless communication with the controller (e.g., via short-range wireless communication protocols).

The artificial heart itself may comprise one or more sensors. For example, one or more sensors within one or more of the valves or pumps may be configured for measuring a blood flow rate, a blood pressure (e.g., a constant fluid pressure, a diastolic pressure, a systolic pressure, and/or the like). The console may comprise one or more pneumatic pressure sensors for sensing pneumatic pressure applied to the various pumps within the patient's body. In other embodiments, the console, the pumps, and/or other electronic components of the artificial heart may be configured for outputting raw signal data indicative of operating characteristics of those electronic components (e.g., to be utilized in a feedback loop for operating the artificial heart). The raw signal data output by electronic components of the artificial heart may encompass data indicative of a driving electrical current (measured in amps, milliamps, microamps, and/or the like), a voltage applied across a pump, an electrical resistance of a component, and/or the like.

An additional sensor may comprise cuff-type blood pressure measurement sensors (or other blood pressure sensors) physically secured at other parts of the patient's body and in wireless communication with the controller. As another example, an additional sensor may comprise an ankle circumference measurement sensor, one or more body temperature sensors (e.g., implanted internal sensors or external sensors secured onto the patient's body), a breathing rate sensor (e.g., monitoring chest movement of the patient), a food consumption sensor (e.g., monitoring movement of the patient's esophagus), a pedometer, a gyroscope (e.g., for detecting the patient's body positioning), an accelerometer (e.g., for detecting movement of the patient's body), and/or the like. In some embodiments, sensors may comprise blood oxygen sensors that may be implanted in the patient's body, $SpO_2$ sensors, carbon-dioxide sensors for monitoring the contents of a patient's breathing expiration, and/or the like.

The sensors are configured to provide raw sensor data or pre-processed sensor data to the controller, such as via an API-based communication channel between the sensor and the controller. The controller is configured to process the received data locally or with remote assistance from the management computing entity 10 (e.g., by passing at least a portion of the received sensor data to the management computing entity 10 for remote processing). Processing the sensor data may comprise providing at least a portion of the sensor data as input to a control parameter model (e.g., a machine-learning model) as discussed in greater detail herein. Sensor data may be provided to the controller periodically or continuously by the one or more sensors, thereby enabling the controller to make real-time adjustments to the operation of the artificial heart based at least in part on the sensor data.

As discussed in greater detail below, the sensor data generated by one or more body sensors and/or generated by the artificial heart itself may be utilized for detecting a trigger condition to be utilized for initializing a safe mode (e.g., implementing safe mode parameters stored locally at the artificial heart or causing the controller to transmit control parameters corresponding to the safe mode parameters instructing the artificial heart to implement the safe mode parameters). For example, upon determining a blood pressure measurement indicative of a severe injury of the patient, the controller and/or the artificial heart may implement a safe mode to slow the rate of circulation of blood within the patient's body until the injury can be closed to minimize the risk of the patient losing significant amounts of blood.

Example System Operation

Figure 4:
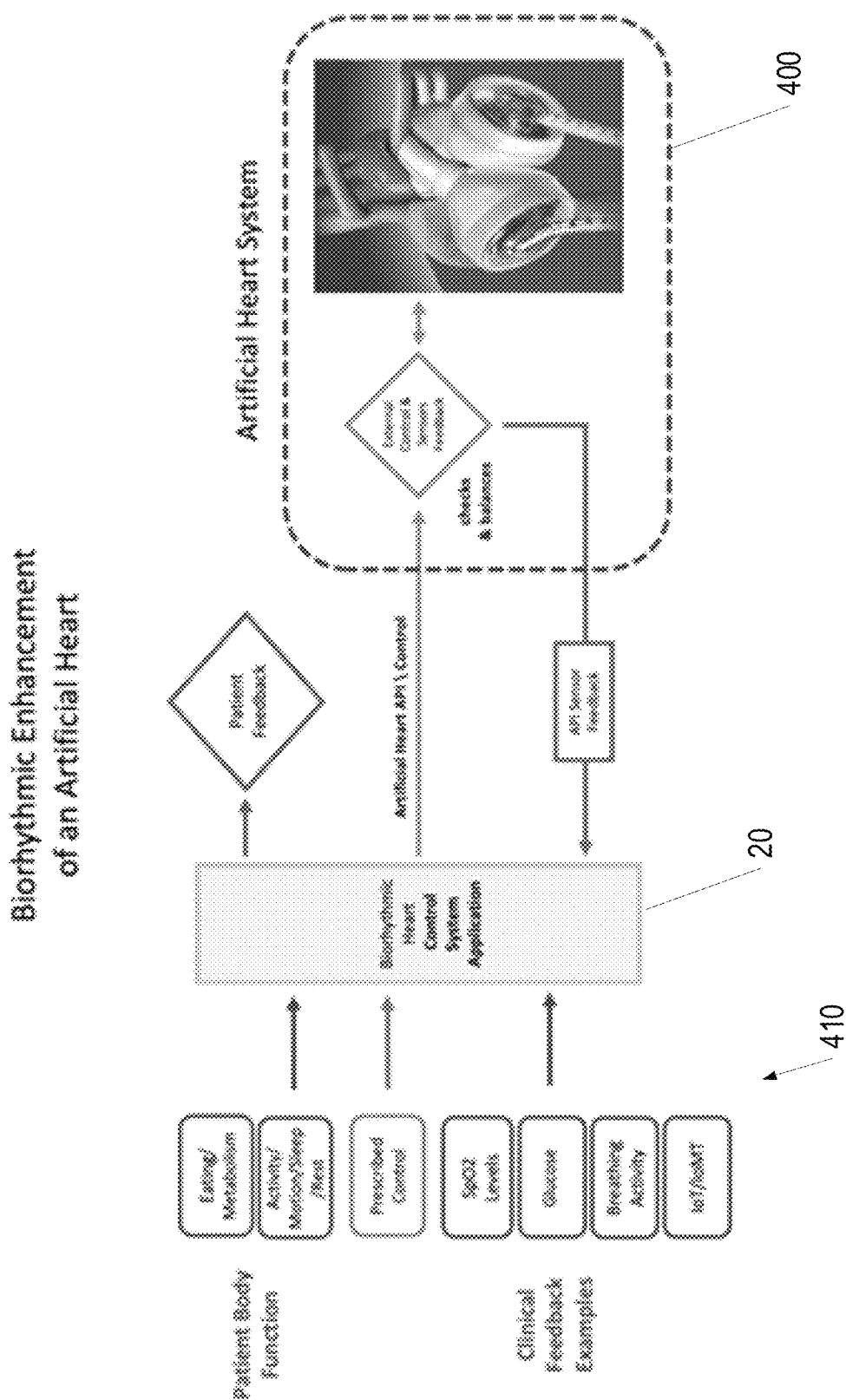
FIG. 4 is a schematic diagram illustrating connections between various components of an artificial heart system according to certain embodiments.
Figure 5:
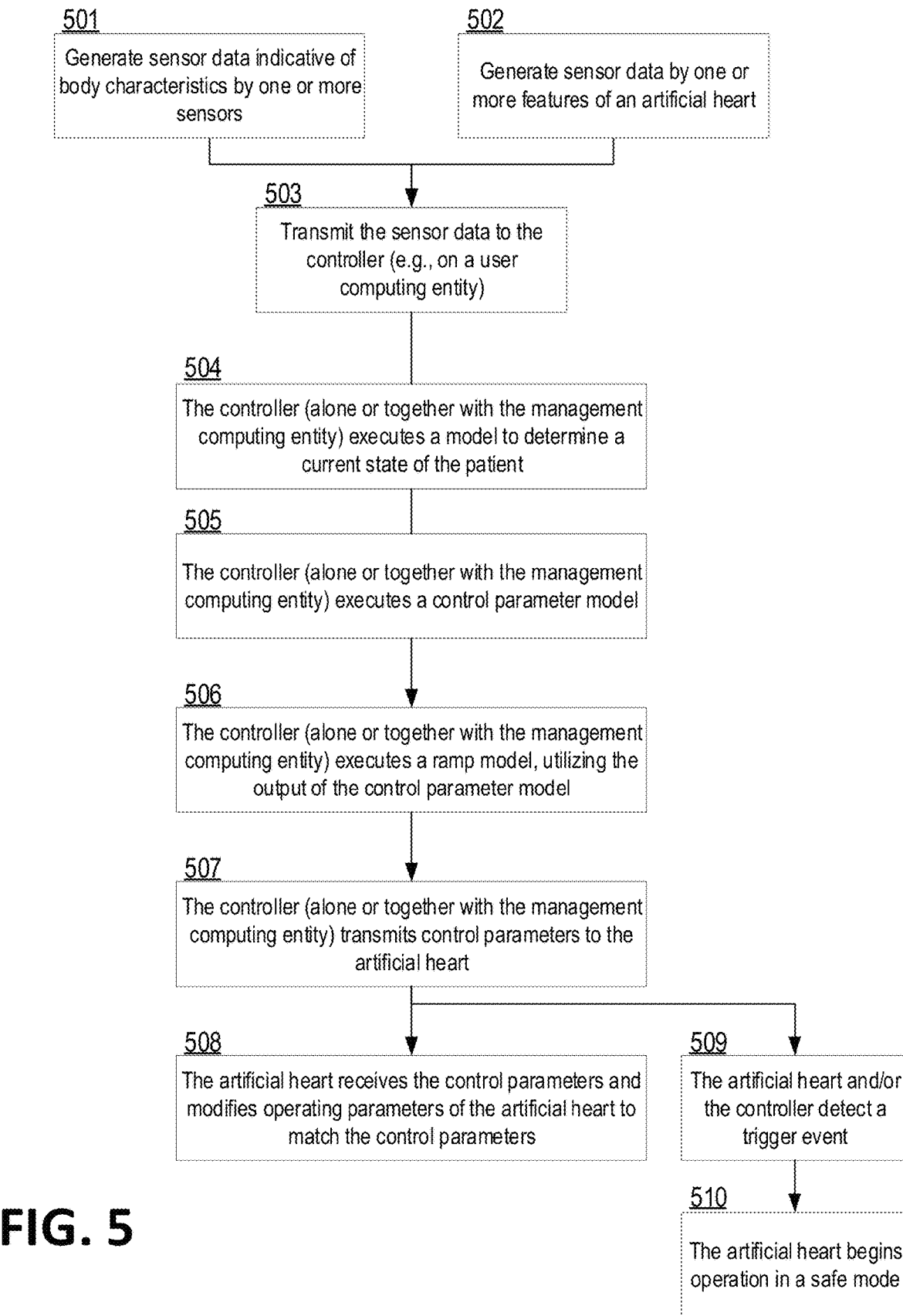
FIG. 5 is a flowchart illustrating steps for adjusting the operational parameters of an artificial heart according to certain embodiments.
Figure 6:
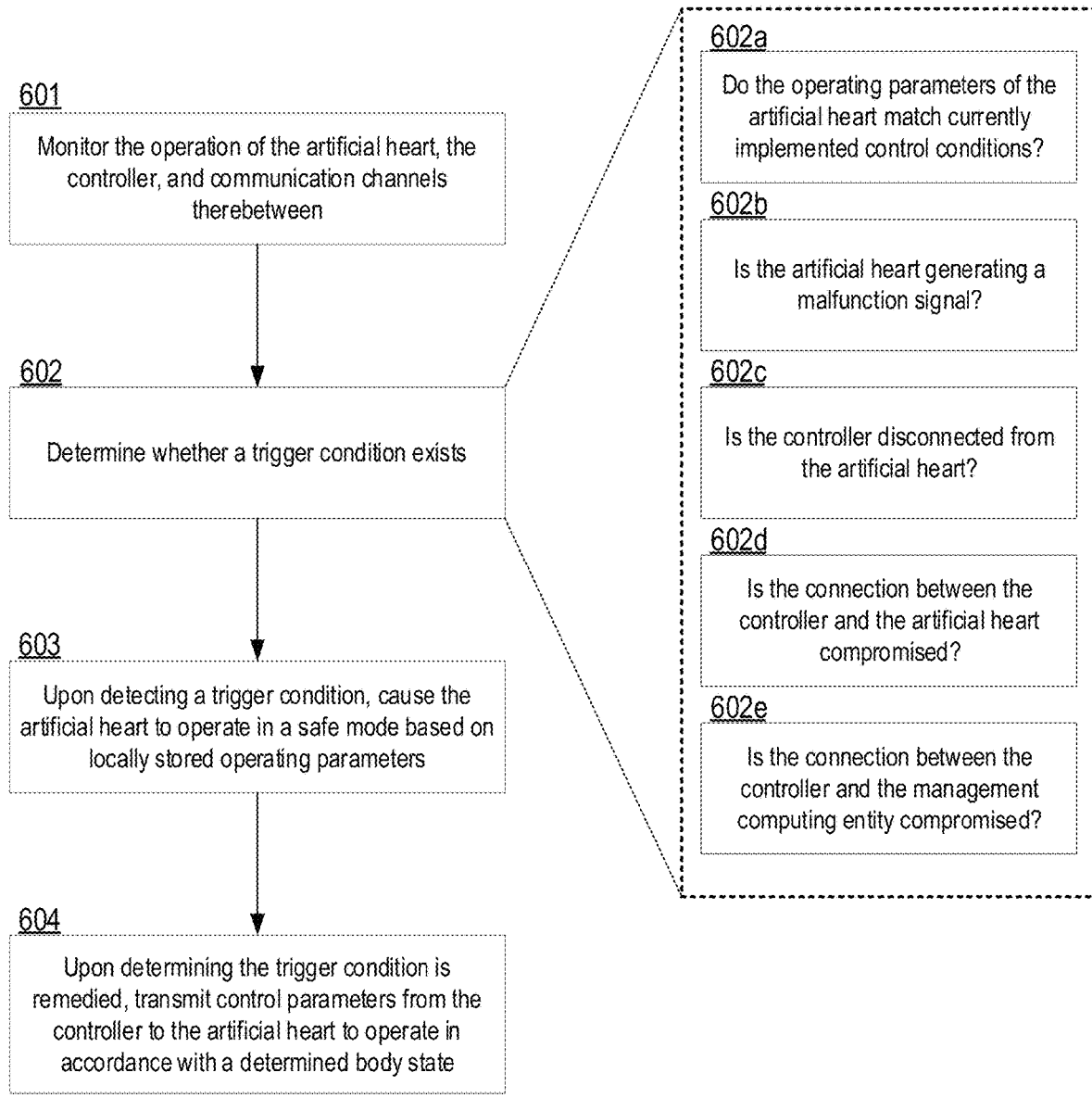
FIG. 6 is a flowchart illustrating steps for implementing a safe mode with an artificial heart according to certain embodiments.

The operation of a system for controlling operation of an artificial heart is described in reference to FIGS. 4-6.

Artificial Heart Control Methodology

An artificial heart system comprises the artificial heart and a controller, and in certain embodiments additionally comprises a remote management computing entity 10 for executing various models in combination with the controller to determine a body state of the patient and/or to determine appropriate control parameters (that are consistent with physician-specified acceptable operation parameters) for the patient.

As mentioned above, an artificial heart of certain embodiments may be controlled via signals generated by a controller (operating alone or in combination with a remote management computing entity 10) and received by the artificial heart, for example, via an API-based communication channel between the controller and the artificial heart. The API-based communication channel enables the controller (which can be implemented as a user computing entity 20, such as a smart phone, a wearable computing entity, and/or the like) to operate with multiple artificial heart types/styles without needing artificial heart-specific programming language for communication of control parameter data to the artificial heart. FIG. 4 schematically illustrates the connectivity and data exchange functionality of the artificial heart system (shown at 400) with the controller (which may be a part of a user computing entity 20, as illustrated in FIG. 4), and various sensors (collectively referred to as 410).

The controller is configured for generating artificial heart control parameter data to be provided to the artificial heart for controlling various functions of the artificial heart by adjusting the currently implemented operational parameters to match the control parameter data. Speed control (e.g., changing the rate of pumping of the artificial heart) is provided by controlling a pulse width of electrical pulses provided to the pump of the artificial heart, by controlling an electrical current level applied to the pump, and/or the like. Linear-based control, such as via ramping for implementing changes in a pump rate, may be implemented to protect against rapid changes in flow to protect the patient's organs. Flow control may also be provided via volume measurement and adjustment (and the artificial heart may include functionality for converting a volume control into signals consumable directly by the pump). For example, volume control and measurement may be implemented via an adjustable chamber width or shape that is readable by a sensor (for a feedback loop of controlling the adjustable chamber width and/or shape) to adjust the flow, independent of the pump rate. Additional signals provided by the controller comprise alerting protocols and/or safety parameter signals and access (e.g., to activate a safe mode of the pump according to certain trigger conditions).

The API-based communication protocol may be one-way (e.g., such that the controller provides control parameter data to the artificial heart). In other embodiments, the API-based communication protocol may be two-way (as illustrated in FIG. 4), such that the controller provides control parameter data to the artificial heart and the controller receives signals generated from one or more body sensors (or other feedback mechanisms) integrated with the artificial heart (e.g., blood measurements from sensors within the artificial heart, such as glucose measurements, nutrient level measurements, blood density measurements, oxygen saturation measurements ($SpO_2$), coagulation property measurements, blood temperature measurements, and/or the like. These sensors (some of these sensors may be a part of the artificial heart system 400) measuring the blood properties within the artificial heart. The controller may additionally receive signals such as artificial heart operational parameters (which may be a part of sensor data received and processed by the controller and/or the management computing entity 10), such as power-level measurements (e.g., indicative of power level stored within an onboard battery or other power source), and/or other operational parameters of the artificial heart).

For controlling a pump rate (or volumetric flow rate), the controller is configured to control the operation of the artificial heart via an API-based communication protocol (it should be understood that artificial heart-specific communication protocols may be alternatively used in certain embodiments). As discussed herein, the controller generates and transmits control parameter data via the API-based communication protocol, which is then received by the artificial heart and the artificial heart adjusts currently implemented operational parameters based at least in part on the received control parameter data.

The API-based connection may be utilized together with artificial hearts operating as electrical-current controlled pumps or voltage-controlled pumps. For voltage controlled pumps, feedback data of the operation of the pump may be provided in the form of data indicative of varying cyclic electrical current levels that vary according to pump rate and varying electrical current rates may be utilized to detect opposition to flow or pressure (back pressure) to enable detection of the elasticity of the venous tissues of the patient's arterial system based at least in part on backpressure measurements over time. Varying voltage levels may be utilized to adjust the operation of the pump for the voltage-controlled pumps.

For pulse control or solenoid-type artificial hearts, the operation of the pump may be monitored over short bursts of voltage measurements at specific intervals, and the pulse width may be adjusted as needed to adjust the pump rate/flow rate of the pump.

The specific operation of the artificial heart may be controlled via hardware/firmware of the artificial heart itself, with the control parameter data being provided from the controller via the API-based communication channel to enable the controller to communicate appropriately with the hardware/firmware of the patient's artificial heart. Analogous control may be provided to pacemakers or other partial heart replacement controllers are implemented.

As discussed herein, the API-based communication channel may be a two-way communication channel, with the artificial heart providing sensor data or feedback data to the controller to assist in operation of the artificial heart. Sensor data may comprise raw sensor data to be interpreted by the controller, or pre-interpreted sensor data that is readily consumable by the controller, such as for providing the data to a control model (e.g., a machine-learning based control model) for determining appropriate control parameter data to be provided to the artificial heart.

Example sensor data comprises fluid (blood) pressure sensor data, which may be analyzed as both forward (during pump operation) and resting pump fluid pressure sensor data in relation to chamber expulsion of blood for sensing blood forward pressure and back pressure flow (indicative of the relaxation of venous tissue). A sinusoidal-type waveform of pressure (indicative of ingress and egress blood flow into the artificial heart) is generated for the artificial heart.

Additional example sensor data comprises a heartbeat (pump interval) sensor indicative of forward fluid movement pressures and/or fluid volumetric flowrates. This data may be analyzed to determine a cyclical pump (pulse) operation of the artificial heart. This is an indicator of the operation of the artificial heart. Alternatively (or additionally) a fluid flow rate for a constant flow model may be monitored as a flow rate of the artificial heart. The flow rate data extracted from the operation of the artificial heart may be supplemented with blood pressure cuff measurement from an external blood pressure sensor, which may be used as input to the control parameter models.

These pressure measurements may additionally be utilized for estimating arterial wall stiffness (also referred to herein as venous tissue flexibility) to further refine data collected indicative of pulse wave velocity (PWV)—the speed at which an arterial pulse propagates along the arterial wall. These measurements encompass a consideration of the flexibility of the aortic valve. Safe levels of flexibility of arterial walls is important to patient safety for ensuring a minimal stroke risk. With an artificial heart, the flexibility of arterial walls does not encompass the flexibility of the aorta. In light of the removal of the aorta, backflow pressure measurement may be utilized as a proxy measurement indicative of the flexibility of the arterial walls, utilizing physician assisted setup and baseline values for the operation of the artificial heart, the controller (and/or the management computing entity 10) correlates electrical current flow to the artificial heart to a determination of arterial flexibility, which may be utilized for establishing safe pressure values for operation of the artificial pump to minimize the patient's risk of a stroke.

In certain embodiments, the artificial heart, in conjunction with the controller, is configured for implementing various safety-based operational parameters that are configured to initialize a "safe mode" set of operating conditions upon the occurrence and detection of one or more specified trigger conditions. The controller periodically or continuously monitors control parameters provided to the artificial heart and operational parameters indicative of the actual operation of the artificial heart to identify potentially problematic operating conditions and/or potentially problematic differences between the control parameters and the operational parameters. For example, the controller is configured to analyze the control parameters, particularly significant changes in the control parameters for validity (to ensure the controller and/or the artificial heart is operating appropriately) and to ensure that the control parameters are being properly passed between the controller and the artificial heart, such as by using checksums (and methodologies for validating checksums provided with the control parameter data) and/or valid parameter ranges for the operational parameters to ensure the communication channel between the controller and the artificial heart has not been compromised (e.g., accessed by an unauthorized third party entity/system). The controller is configured to reject (or otherwise not implement) faulty, non-logical, or known problematic parameters that could harm the patient. Moreover, these safety-based operational parameters ensure the artificial heart continues operating (at least in a safe-mode) if the controller is lost, loses power, or otherwise loses connection with the artificial heart (e.g., when the controller is implemented as a user computing entity 20 that may be misplaced or lose power, independently of the operation of the artificial heart). Moreover, the safe mode parameters may be implemented in the event of certain sensor data signals, such as blood pressure (or other signals) indicating the patient has a severe injury and is losing blood through the injury. Moreover, the safety-based operational parameters may be saved as a backup via memory storage areas accessible to the management computing entity 10, which may operate as a "cloud"-based computing system accessible via the internet, such as by the controller. The backups may enable the controller to be replaced without requiring the arduous undertaking of re-establishing control parameters and/or operational parameters of the controller and/or artificial heart.

Sensor Data Collection

Control of the artificial heart may be based at least in part on data generated by one or more body sensors and collected by the controller and/or the remote computing entity 10. Sensor data may be generated and provided to the controller from one or more sensors (inclusive of sensors integrated with the artificial heart, as discussed above). The sensors may be external to the patient's body or implanted within the patient's body. The sensors may be in communication with the controller via any of a variety of control mechanisms. Particularly for those embodiments in which the controller is implemented as a mobile computing entity (e.g., a smart phone) or implemented as an app executing on a mobile computing entity, one or more sensors of the patient may communicate with the user's mobile computing entity in a manner to be consumed by a separate application executing on the mobile computing entity. The controller may be configured to access the sensor data consumed by the separate application (e.g., after the patient/user provides appropriate access permissions to the computing entity). It should be understood that the sensors may communicate with the controller via any of a variety of communication protocols and/or communication channels. The sensors may communicate wirelessly with the controller (e.g., via Bluetooth or other short-range wireless communication protocols). The sensors may alternatively or additionally communicate via wired communication with the controller. In other embodiments, the sensors may be integrated into the device of the controller (e.g., a user's mobile computing entity executing the controller application may comprise one or more sensors, such as a gyroscope, accelerometer, GPS sensor, camera, and/or the like), and such signals may be provided to the controller application via communication channels that are entirely onboard the mobile user computing entity 20.

Additional example sensor data may comprise data indicative of a pressure (or dimensional measurement of diameter, circumference, or the like) of a patient's ankle, as generated by a sensor device integrated into a sock or other wearable device. Such sensor data is indicative of swelling of the patient's ankle, which may be usable for detecting edema and/or blood flow intervals (pulse) within the patient's lower extremities. Sensor data may additionally comprise oxygenation sensor ($SpO_2$) data, breathing rate data (e.g., oxygen intake rate and/or sympathetic levels of effort expended during inspiration and expiration), glucose levels indicative of glucose rate of metabolism (dependent on comorbidities), ketone levels indicative of liver function, other data generated by Internet of Things (IoT)-based sensors, such as data indicative of heart health, swelling, edema, and/or the like. Sensor data may additionally comprise data indicative of mechanical operation of the artificial heart, such as mechanical pump characteristic measurements of the artificial heart. In certain embodiments, sensor data may comprise sensor data generated for monitoring signals within a Vagus nerve of the patient. As yet other examples, sensor data may comprise sexual proximity data indicating a proximity to a sexual partner that is indicative of sexual activity. Other sensor data examples encompass mental stress sensor data generated by mental activity sensors, simulated inputs provided to the patient's body that may be externally controlled (e.g., by a physician), internal body temperature sensor data from sensors implanted at various locations within the patient's body, $CO_2$ sensor data of a sensor for monitoring the content of a patient's expelled breath, Ketosis sensor data from sensors monitoring characteristics of a patient's blood and/or breath, and/or the like.

As discussed herein, the sensor data is provided as input to various models (e.g., the control parameter model, the ramp rate model, and/or the like) to establish appropriate control parameters to be provided to the artificial heart for controlling the operational parameters thereof, in real-time.

Setup

Operation of the artificial heart is established for a specific patient, and therefore the operational parameters and control parameters are established during an initial setup for the patient. Setup may occur prior to, during, or following implantation of the artificial heart in the patient. It should be understood that analogous setup and/or other methods and features/configurations as discussed herein may be utilized with a partial artificial heart replacement (e.g., a pacemaker) configured to assist the normal operation of the patient's natural heart.

The management computing entity 10 is configured to generate and provide one or more interactive setup graphical user interfaces (GUIs) to a user computing entity 20 to facilitate setup of the controller and/or the artificial heart. The one or more interactive graphical user interfaces comprise a plurality of prompts and associated editable text fields in which the physician (or another user) provides minimum and maximum acceptable operational parameters for the artificial heart for one or more patient states (e.g., detected activities of the patient as determined at least in part on sensor output of the plurality of body sensors of the patient).

In certain embodiments, the management computing entity 10 pre-populates one or more of the editable text fields within the setup GUIs with recommended values. The recommended values may be patient specific, and may be generated based at least in part on patient data stored within a patient profile accessible to the management computing entity 10. In certain embodiments, the recommended values may be established to emulate baseline values determined or estimated by the management computing entity, for example, utilizing a baseline model (e.g., a machine-learning model) configured to review patient-specific data within a patient profile (e.g., electronic medical records data stored as a part of the patient profile that includes data regarding the operation of the patient's heart prior to the need for a heart replacement) and to generate one or more recommended values specific to the particular patient.

In other embodiments, the recommended values may comprise values identified as recommended values for a plurality of patients. In certain embodiments, the recommended values may be standard values for any patient satisfying one or more baseline criteria. The baseline criteria may comprise age data (e.g., all patients of a particular age are assigned the same recommended values). The baseline criteria may comprise additional criteria, such as age criteria, certain comorbidity criteria, and/or the like.

In certain embodiments, the patient states may be customizable for individual patients. As discussed herein, patient states may be reflective of particular activities (e.g., exercising, sleeping, eating, and/or the like), however the patient states may reflect other attributes of the patient that are not directly tied to particular activities. As examples, a patient state may be a determination that an ankle circumference is determined (via appropriate sensors) to be 20 inches (within a 0.25% tolerance), and the minimum and maximum flowrates (defining acceptable operational parameters for a particular patient state) for the artificial heart under these conditions may be established (by the physician) as $40/150$ (for pulse interval artificial hearts) or 3-8 L/min (for continuous flow artificial hearts). It should be understood that a single sensor measurement may be utilized to establish a patient state (as reflected with the above example) or multiple sensor measurements may be utilized to establish a patient state. As another example, a particular patient state with assigned minimum and maximum flow rates may be characterized by an $SpO_2$ level between 80-98, a breathing rate between 12-18 breaths per minute, a glucose level between 75-150 mM, and ketone levels between 1.5-3 mmol/L.

Upon receipt of user input indicating that minimum and maximum flowrates have been established for each patient state, the management computing entity 10 communicates these physician-provided/approved acceptable operational parameters to the controller for implementation with the artificial heart during use. As discussed in greater detail herein, the management computing entity 10 provides the acceptable operational parameters to the controller such that the controller can communicate applicable operational parameters to the artificial heart via an appropriate communication channel (e.g., an API-based communication channel), without requiring internet connectivity of the controller and/or the artificial heart.

Moreover, it should be understood that the setup methodology may be accessible and repeatable as necessary. For example, a physician may periodically review the acceptable operational parameters assigned to a particular patient in light of sensor data collected for the patient, and may provide updated acceptable operational parameters to be utilized when generating control parameters after the acceptable operational parameters have been updated.

Physician-Prescribed Operational Parameters

The initial setup procedures are conducted based at least in part on input from a patient's physician. It should be understood that the operation of the artificial heart (including the generation of the control parameters and the adjustment of operational parameters based at least in part on those control parameters) may be periodically reviewed and/or adjusted, for example, based at least in part on input from the patient's physician, such as to update acceptable operational parameters for various patient states. During initial setup, the physician provides input via a user interface of a user computing entity 20 in communication with the controller of the artificial heart and/or in communication with the management computing entity 10, which provides appropriate data to the controller such that the controller may implement the data to generate and/or provide control parameter data to the artificial heart based on a detected state of the patient's body/activity. The physician input may encompass a maximum and/or minimum flowrate for the artificial heart for one or more body activities. In certain embodiments, the management computing entity 10, which provides and/or manages the content of the user interface provided to the physician's user computing entity 20, auto-populates recommended maximum and/or minimum values for flow rates for various activities. The recommended maximum and/or minimum values may be established based on historical data for a plurality of patients. The historical data to be utilized in establishing recommended maximum and/or minimum values may be selected to correspond to patients having similar health conditions as the current patient (similarities in health conditions may be established via a machine-learning based clustering analysis, considering data within electronic medical records (EMRs) of the patients). The historical data may alternatively be non-specific to the current patient and may encompass historical data for all patients for which data is available. The recommended values may be modified by the provision of user input provided by the physician to provide maximum and/or minimum values of flow rate for various activities that are specifically tailored to the patient, based at least in part on the physician's professional judgment.

As discussed herein, the operation of the artificial heart, including the generation of control parameters by the controller, may be monitored and recorded by the management computing entity 10, for example, within a profile corresponding to the patient. The controller is configured to transmit data indicative of the control parameters to the management computing entity 10 for storage within the patient profile. The patient profile may be linked with (or a part of) the patient's EMR data, which may be accessible by the patient's physician. The patient's physician may additionally be granted access, via the management computing entity 10 to control of the control parameters corresponding to the patient remotely, such as via data access to the patient's profile as stored by the management computing entity 10. Thus, the patient need not visit the physician in person to enable the physician to adjust the operation of the patient's artificial heart. Thus, the patient's physician may adjust the maximum and/or minimum values of flowrate for various activities remotely, for example, upon determining that data within the patient's profile indicates that the patient's bodily function is limited or otherwise not optimized utilizing previously prescribed control parameter limitations and/or upon determining that a change to the patient's health conditions, medications, and/or the like has occurred that warrants a change to the control condition limitations applicable to the patient.

Dynamic Artificial Heart Control

The controller is configured to control the operation of the artificial heart to at least substantially emulate the operation of a typical heart by responding to the patient's bodily functions and activities (to the extent possible based on the sensor data available to the controller), while staying in compliance with any physician-specified functional limitations established during an initial setup procedure as described above (or established during a later adjustment setup procedure). The controller relies on sensor data received from the various sensors monitoring bodily functions of the patient's body to identify activities of the patient, thereby enabling selection of appropriate control parameters for execution by the artificial heart.

Body activities are identifiable based on characteristic bodily responses that may be detectable by the one or more body sensors that are in communication with the controller. Some body activities may be identified based on the output of a single sensor, while other body activities can be identified based on the combined output of multiple sensors. For example, digestion may be characterized by an increase in body temperature together with irregular (or non-existent) indications of patient movement (e.g., from an accelerometer). Other sensor output may additionally be utilized for identifying digestion bodily functions (e.g., monitoring blood content for nutrients). Vigorous exercise may be characterized by an increase in body temperature together with an increase in breathing rate and an indication of regular bodily movement (e.g., from an accelerometer). However, the human body does not operate in a manner of cleanly distinguishing between discrete "activities," and instead all of the body's functions vary along a continuum. For example, blood glucose levels may vary and change in slight increments nearly continuously, and distinctions between a blood glucose level indicative of a digestion functionality of the human body are distinguishable from other bodily functionality merely based on assigned threshold values for blood glucose levels (those threshold values are generally established based on extensive research for distinguishing between bodily states). In certain embodiments, the identification of various bodily functions is performed in accordance with a body function model, such as a machine-learning based model trained via supervised machine learning and a training data set providing sensor output corresponding with various bodily activities. The body function model is configured to distinguish between various body states of the patient, in real-time, such that the controller can select the appropriate ranges of control parameters that are currently applicable to the artificial heart at any given time.

The training data of the body function model may be supervised by tagging of specific time periods (the sensor data from each of a plurality of sensors for a particular patient are characterized with time data providing timestamps indicative of times when particular data is generated) as being reflective of particular bodily activities and/or body states. The training data may be patient-specific and may be generated within a controlled setting, such as by monitoring the sensor output while the patient undertakes a series of tasks, such as eating, walking, running, resting, sleeping, and/or the like, or the training data may comprise data from a plurality of patients, thereby providing a more expansive training data set that may be utilized to characteristically identify particular periods of patient activity.

As discussed above, the initial setup data may correlate particular artificial heart control parameters with particular identified patient activities. Thus, upon identifying a particular activity being undertaken by a patient (alternatively referred to as identifying a patient's body state), the controller identifies and applies appropriate control parameters to the artificial heart, such that the artificial heart provides appropriate blood flow to the patient's body to accommodate the patient's body state.

More specifically, the initial setup parameters for a patient may correlate an exact set of control parameters to a bodily activity. In other embodiments, allowable control parameters for particular bodily activity established within the initial setup may encompass a range of allowable control parameters. Selection of a precise control parameter within the range of allowable control parameters may be based at least in part on the output of a control parameter model (e.g., a machine-learning based control parameter model) trained utilizing patient-specific data (for a single patient) to enable selection of a precise control parameter for application of the current state of the patient.

The patient may be provided with a level of permissible manual control of the control parameters, such as through a user-interface of the controller, a button on a separate device in wireless communication with the artificial heart, or a user interface feature (e.g., a button) on a component of the artificial heart (e.g., the console) located external to the patient's body that provides a "boost" functionality that increases the flowrate of the artificial heart (within a defined level, such as up to a 5% increase while remaining within permissible ranges of control parameters for the particular patient body state as established during initial setup) or a "decrease" functionality that decreases the flowrate of the artificial heart (within a defined level, such as up to a 5% decrease while remaining within permissible ranges of control parameters as established during initial setup). Data indicative of the patient's use of the boost and/or decrease functionality may be utilized for refining the control parameter model for the particular patient, so as to provide precise and customized operation of the artificial heart tailored to the needs of the particular patient. For example, patterns may be identified between the patient's use of the boost and/or decrease functionality and particular sensor outputs to customize the automatic application of control parameters to the artificial heart. In certain embodiments, the use of the boost and/or decrease functionalities may cause a notification to be provided to the patient's physician to review the initial setup parameters for an adjustment to the permissible ranges of operation of the control parameters.

The control parameter model may be continuously refined as sensor data is utilized within a feedback loop both for generating control parameters and for monitoring the effectiveness of applied control parameter data on the patient's bodily function. For example, periods of mild elevated glucose levels (within a defined range, above a threshold, and/or the like) may be indicative of digestion. The operation of the controller (and the control parameter model) may be refined over time based on detected periods of fasting and detected periods of digestion to identify heartrate stimulus levels needed to facilitate metabolism of the patient. Other sensor data may be utilized during such periods of refinement as well, such as sensor data indicative of food consumption, exercise, sleep, intimacy, and/or other sensor data indicative of the operation of the sympathetic nervous system (e.g., indicative of signals within the vagus nerve, such as signals received directly from sensors monitoring the activation of a vagus nerve system, such as a portion of a vagus nerve located proximate the patient's heart, such as via an electro-impulse measurement sensor).

Responsive Ramping During Dynamic Control Changes

The human body does not naturally cause drastic and sudden changes in the operation of internal organs, including the heart. Instead, changes in operation, which may be deemed necessary to accommodate changes in the body's activity level, occur gradually, over a "ramped" transient period (e.g., during a gradual increase in blood flow rate or a gradual decrease in blood flow rate). To emulate the typical operation of the human body, the controller works together with the artificial heart to provide appropriate ramp rates (rates of change) for changing flow rates of the artificial heart upon a determined need for changing the operational parameters of the artificial heart.

A ramp model (e.g., a machine-learning model trained via patient-specific data) is utilized for establishing an appropriate ramp rate between changed operational parameters. As mentioned above, those operational parameters are identified and applied via a control parameter model, and therefore the ramp model and the control parameter model operate in concert (e.g., the output of the control parameter model is fed as input to the ramp model) so as to establish both the appropriate operational parameters and the appropriate ramp rate for transitioning between operational parameters when the controller determines that a change in the operational parameters is deemed appropriate.

In analyzing ramp rates and/or for establishing an appropriate ramp rate for transitioning between operational parameters of the artificial heart, the controller (via received sensor data) analyzes pressure data upon each initial pump cycle of a particular established set of operational parameters, for example, to detect/estimate a flexibility of venous tissues of the patient, such that the controller identifies appropriate ramp rates between operational parameters that protect the patient's organs and tissue and minimize the patient's risk of a stroke. These ramp rates and the desired changed operational parameters are prior to beginning a transition to the desired changed operational parameters, thereby enabling the controller (through appropriate modelling) to plot the targeted flow rate and changes in flow rate to reach the desired changed operational parameters.

For continuous flow artificial hearts, sensor data of flow pressure measured immediately following changes in flow-rate may be utilized for detecting/estimating a flexibility of venous tissues of the patient, as these initial nearly-transient periods of operation provide adequate backflow within the venous tissues to enable an estimation of the level of flexibility of the patient's venous tissues.

Moreover, the ramp rate model may be further configured for monitoring the ramp rate as it is applied by the artificial heart, and to generate a trigger signal utilized by the controller for initiating a safe mode upon detection of significant ramp pressure changes (which may be indicative of an abnormal body condition).

In certain embodiments, training of the ramp rate model may further consider patient feedback (as reflected in FIG. 4), such as patient feedback indicating whether any abnormal or uncomfortable sensations were noticed during any transitions between operational parameters of the artificial heart (e.g., pain, an unexpected loss of breath, and/or the like). This subjective data of the patient's thoughts/feelings may be used to further refine and establish ramp rates that are comfortable for the patient.

As an example operation of the ramp rate model, the ramp rate model may provide an appropriate ramp rate for exiting a sleep mode (to be used while the patient is detected to be asleep), including mid-ramp localized peaks and localized valleys in flow rate. For example, the ramp rate model may establish a ramp rate encompassing a slight increase in heart rate while the patient is first awakening (mimicking an initial "boost" that a normally functioning heart would provide) followed by completion of the ramp period until reaching a steady-state for the patient after initially awakening. Such determinations of the appropriate ramp rate for a period of awakening is determined based at least in part on an analysis of monitored signals of sleep patterns, movement, and/or the like.

Safe Mode Operation

The artificial heart system (the artificial heart together with the controller) is configured to operate in a safe mode to protect the patient's body and blood supply upon the occurrence of one or more safe mode trigger conditions. Control parameter data for the safe mode may be stored locally on the memory storage areas of the artificial heart, such that external communication with other computing entities is unnecessary for implementation of the safe mode. For example, the safe mode may be utilized when communication between the controller and the artificial heart is interrupted (e.g., if the controller is misplaced or broken or if the power supply of the controller diminishes), or when certain pressure changes are detected within the artificial heart that are indicative of significant blood loss from an injury to the patient. The safe mode may thus provide a flow rate of blood at a minimum viable flowrate for the patient to deliver blood to the patient's organs, without increasing the blood flow rate to accommodate other activities (unless and until the trigger condition is remedied). The flowrate and/or other operational parameters of the safe mode may be established by a physician of the patient. A trigger condition may additionally comprise a determination that the artificial heart itself is malfunctioning. For example, a communication interface of the artificial heart may be incapable of communicating with a controller, such that the safe mode should be implemented to maintain at least a minimum viable blood flow rate within the patient via the artificial heart. As yet another example, a determination that the artificial heart is malfunctioning (e.g., a self-determination, by a processor of the artificial heart) may be determined upon detecting a deviation between the control parameters utilized to establish currently-utilized operational parameters and the operational parameters reflecting the current operation of the artificial heart. Such a deviation may indicate that the pumps, valves, or other hardware of the artificial heart are incapable of maintaining a flow rate to match the desired operational parameters (established based at least in part on the control parameters).

FIG. 6 is a flowchart illustrating an example process for implementing a safe mode. As reflected at Block 601, the controller is configured to constantly monitor for sensor data indicative of various trigger conditions. In certain embodiments, the artificial heart is additionally configured to self-monitor generated sensor data to identify potential trigger conditions (and to monitor the connection between the artificial heart and the controller). Each of the controller and/or the artificial heart itself is configured to monitor data indicative of the operation of the hardware of the artificial heart to detect potential malfunctions of the artificial heart hardware, that may be identified as trigger conditions to implement the safe mode. Even for those embodiments in which the artificial heart has limited onboard processing resources, the artificial heart may have adequate onboard memory and processing resources to detect a safe mode trigger condition and to invoke operation of the artificial heart in the established safe mode.

As indicated at Block 602, one or more devices within the artificial heart system (e.g., the controller or the artificial heart itself) may detect a trigger condition. As reflected within the non-limiting examples of Blocks 602*a*-602*e*, the system is configured to transition into a safe mode upon the occurrence of one or more alternative trigger conditions. In certain embodiments, a trigger condition may be a detection of sensor data indicative of a low venous flexibility. As another example, a trigger condition may be a detection of significant differences in blood flow as reflected by current flow measurements within the artificial heart. For example, an increase in blood flow or a decrease in electrical current necessary for application to the artificial heart to achieve a desired flow rate may be indicative of a decrease in fluid pressure within the patient's arteries and veins, which itself may be indicative of a significant injury allowing blood to flow out of the patient's body (thereby decreasing backpressure that would be characteristic of a closed blood flow system).

In certain embodiments, a safe mode trigger condition may encompass a detection of potentially nefarious interference with the operation of controller and/or the artificial heart, which may be detected based at least in part on the determination that the artificial heart, the controller, the management computing entity 10, or a communication channel between one or more of the computing entities has been compromised. For example, a determination that unrecognized signals are detected within the one or more communication channels may be indicative of a trigger condition. In certain embodiments, the artificial heart and/or the controller may be in communication with proximity sensors for detecting potentially nefarious sources of interference signals, such as radio-frequency (RF) sensors, or other signal wave sensors. Upon detection of interference signals, the controller may provide a notification to the patient. If the controller and/or artificial heart detect interference that may cause potential interruption in the communication between the controller and the artificial heart, the artificial heart may transition to a safe mode, and may specifically operate based on data stored locally at the artificial heart, thereby ensuring interference does not cause an undesired change in operation of the artificial heart.

As yet other examples, a trigger condition may encompass a determination (e.g., by the artificial heart) that a connection between the artificial heart and the controller has been disconnected. For example, the communication interface of the artificial heart may malfunction, the communication interface of the controller may malfunction, the controller may power-down (e.g., when an onboard power supply has expired), and/or the like. The artificial heart continues operation by switching to the safe mode until a communication with the controller can be reestablished.

In certain embodiments, the onboard processing resources of the artificial heart monitor the operation of the various hardware components thereof. Upon a determination that one or more components is malfunctioning, the artificial heart may generate a malfunction signal. The malfunction signal may be a generic malfunction signal indicating the artificial heart should be diagnosed to determine what hardware component is malfunctioning. In other embodiments, the malfunction signal encompasses data specifically identifying the determined malfunction, to facilitate diagnosis and repair of the artificial heart. Upon generation of the malfunction signal, the artificial heart may transition to safe mode until the malfunction is remedied.

As explicitly indicated at Block 603 of FIG. 6, the artificial heart transitions to the safe mode operation, utilizing locally stored operational parameters for operation of the safe mode so that communication with the controller is unnecessary (as the communications with the controller may be unsecured, unavailable, or faulty). In other embodiments, the controller provides control parameter data reflective of parameters of the established safe mode of operation. By providing the control parameter data reflective of the safe mode of operation to the artificial heart, the controller causes the artificial heart to implement the safe mode of operation.

The artificial heart system is configured to adjust the operation of the artificial heart (by adjusting the currently implemented operational parameters) based on control parameter data transmitted to the artificial heart from the controller upon determining that the trigger condition has been remedied, as reflected at Block 604. In certain embodiments, the artificial heart, the controller, and/or the management computing entity 10 are configured to automatically determine that the trigger condition has been remedied, for example, by continuing to monitor the operation of the artificial heart, the controller, the management computing entity 10, and communication channels therebetween.

In other embodiments, the artificial heart system requires manual intervention (e.g., in the form of user input) by a user to return to normal functionality of the system, utilizing control parameters transmitted from the controller to the artificial heart to modify the operational parameters of the artificial heart based at least in part on sensor data generated by one or more body sensors monitoring characteristics of the patient's body. Such user input may be provided via a user interface generated and/or displayed via the controller (e.g., a user computing entity 20 providing functionality of the controller).

Illustrative Example of Use

To provide a complete overview of the described functionality, FIG. 5 is a flowchart illustrating operation of a controller in combination with an example artificial heart according to one example set of operations. The artificial heart operates constantly to circulate blood through the patient's body. The operations of FIG. 5 illustrate functionality for modifying the operating characteristics of the artificial heart (e.g., the flow rate) in response to changes in the patient's body state and/or activities.

As the artificial heart is operating in accordance with a first set of operating characteristics, one or more sensors (referred to at 410 in FIG. 4) generates sensor data indicative of characteristics of the patient's body, as indicated at Block 501. In certain embodiments, the artificial heart itself may comprise one or more sensors, or the operating components of the artificial heart (e.g., the pumps, valves, and/or the like) may provide data indicative of the operation thereof, such as data indicative of electric current draw, voltage across the component, and/or the like. This data is generated by the artificial heart, as indicated at Block 502.

The sensor data is provided to the controller, as indicated at Block 503. The sensor data may be provided through appropriate communication channels for communicating between the sensors and the controller. These communication channels may encompass wireless communication channels, such as via short-range wireless communication protocols (e.g., Bluetooth). For other sensors and/or other configurations, the communication channels may be wired communication channels, or the communication channels may be entirely within the hardware of the controller (e.g., within a user computing entity 20 providing functionality of a controller). The communication channels may utilize any of a variety of communication protocols, such as API-based communication protocols or other real-time data exchange communication protocols. The communication protocols may be one-way, such that the sensors only provide data to the controller, or two-way such that the controller may provide data back to the sensors (e.g., to control the operation of the sensors).

Although not shown in FIG. 5, in certain embodiments the controller provides the sensor data to a remote management computing entity 10 to facilitate operation of certain functionalities of the systems discussed herein. As discussed, the management computing entity 10 may be embodied as a cloud-based computing entity with increased processing capacity as compared with a user computing entity 20. Thus, the management computing entity 10 may be configured for generating, training, and/or executing various models (e.g., machine-learning models), and therefore the controller provides the sensor data to the management computing entity 10 for use as input data to one or more models.

The one or more models comprise a model for determining a current state of the patient's body. A determination of the current state of the patient may comprise assigning a state indicator to the current status of the patient, such that appropriate control parameters relating to the state indicator may be determined and utilized to establish appropriate control parameters and/or ramp parameters to be utilized with the patient.

Based at least in part on the received sensor data (from the one or more sensors and/or from the artificial heart) and/or the determined state of the patient's body, the controller and/or the management computing entity 10 executes a control parameter model (as indicated at Block 505) to determine the most appropriate operational parameters of the artificial heart in light of the real-time, current sensor data received for the patient. The output of the control parameter model is one or more control parameters that are to be provided to the artificial heart to enable the artificial heart to modify the applied operational parameters to match the provided control parameters. Ultimately, the control parameters are utilized to establish a second set of operating characteristics of the artificial heart.

The control parameters may be selected for application based at least in part on maximum and minimum pump rates assigned to each of a plurality of patient states (having corresponding state identifiers) by the patient's physician. As an example, TABLE 1, below, provides example heart pump rates to be implemented (without a range of rates) for various states of a patient. The heart pump rates of TABLE 1 are provided as generic heartrates for patients at various ages. It should be understood that the heartrates provided as available control parameters may be patient-specific and may be established based at least in part on medial data specific to the patient.

TABLE 1

| | Activity/State | 20 Years | 40 Years | 50 Years | 60 Years |
|---|---|---|---|---|---|
| Thresholds (Physician specified) | Beats Per min (50-85%) | 100-170 | 90-153 | 85-145 | 80-136 |
| | Avg Max Rate (100%) | 200 | 180 | 170 | 160 |
| Activities | Resting Rate | 75 | 65 | 55 | 50 |
| | Walking Rate | 80 | 90 | 100 | 105 |
| | Running | 120 | 125 | 130 | 140 |
| | Gardening/housework | 77 | 68 | 58 | 60 |
| | Eating | 80 | 85 | 87 | 88 |
| | Shopping | 80 | 90 | 100 | 105 |
| | Swimming | 120 | 125 | 130 | 140 |
| Conditions | Bleeding | Avg | Avg | Avg | Avg |
| | Overdose | Max | Max | Max | Max |
| | Injury | Max | Max | Max | Max |

TABLE 2, below, provides another example of operational parameters available for various patient activities/body states. The data of TABLE 2 provides maximum and minimum heart rate values for various body states, and the exact heart rate for application in the control parameters is to be established within the established ranges by appropriate models. Again, the data of TABLE 2 is provided for multiple patients, distinguished based on age, although it should be understood that analogous ranges of appropriate heart rates may be established for individual patients.

TABLE 2

| Age | Activity | Beats/Min (minimum) | Beats/Min (maximum) |
|---|---|---|---|
| 20 | Resting | 74 | 76 |
| 20 | Walking | 78 | 80 |
| 20 | Running | 115 | 125 |
| 40 | Resting | 62 | 65 |
| 50 | Swimming | 128 | 130 |

However, the artificial heart should not suddenly change the operational parameters thereof, as sudden changes in blood flow may harm the patient (e.g., by causing a stroke). Therefore, as indicated at Block 506, the controller and/or the management computing entity 10 executes a ramp model utilizing data indicative of the first set of operating characteristics of the artificial heart and data indicative of the control parameters generated by the control parameter model to determine an appropriate ramp rate for adjusting the operation of the artificial heart to match the control parameters. In certain embodiments, additional data may be utilized as input data for the ramp model, such as at least a portion of the sensor data generated as reflected at Blocks 501-502. The resulting output of the ramp model is ramp parameters that define a rate of change for implementing the control parameters with the artificial heart.

As indicated at Block 507, the resulting control parameters and ramp parameters are provided by the controller to the artificial heart via an appropriate communication channel. The communication channel may be a wireless communication channel implementing an appropriate communication protocol, such as an API-based communication protocol enabling real-time exchange of data (particularly real-time provision of data from the controller to the artificial heart), thereby enabling the controller to provide the control parameters and the ramp parameters to the artificial heart in real-time, such that the control parameters and ramp parameters may be implemented while the sensor data remains relevant (e.g., immediately after the sensor data is generated), such that the operation of the artificial heart can be changed to reflect a current activity of the patient and/or current body functions of the patient.

As indicated at Block 508, the artificial heart receives the control parameters and the ramp parameters and implements these received parameters to modify the currently implemented operational parameters to match the control parameters, at a rate established by the ramp parameters. However, both the controller and artificial heart monitor for various trigger conditions for transitioning to a safe mode (according to which the artificial heart operates at a constant set of operational parameters that are unaffected by sensor data), such as a disconnection of the communication channel between the controller and the artificial heart, a determination that signals received at the artificial heart from the controller are inconsistent with control parameters and ramp parameters generated in accordance with the control parameter model and the ramp model (which may be indicative of signals generated with nefarious intentions by an unauthorized, external computing entity). As reflected at Block 509-510, if the artificial heart and/or the controller determine that a trigger condition has occurred (e.g., instead of detection of signals appropriately transmitted between the controller and the artificial heart), the artificial heart transitions to operation in the safe mode. The artificial heart may continue operating in the safe mode until the trigger condition is no longer detected. In other embodiments, the artificial heart may continue operating in the safe mode until a physician (or other user) manually resets the artificial heart and/or the controller.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
   receiving, by one or more processors, user input associated with a patient;
   receiving, by the one or more processors, sensor data generated by one or more body sensors monitoring a body of the patient;
   identifying, by the one or more processors and based at least in part on the sensor data and the user input, target operational parameters for an artificial heart;
   determining, by the one or more processors and based at least in part on a control parameter model, control parameters for the artificial heart to achieve the target operational parameters, wherein the control parameter model correlates the control parameters and the target operational parameters based at least in part on the sensor data;
   determining, by the one or more processors and based at least in part on the control parameters and current operational parameters of the artificial heart, a ramp rate for implementing the control parameters by the artificial heart; and causing, by the one or more processors, the artificial heart to implement the control parameters to achieve the target operational parameters according to the ramp rate in real-time.

2. The method of claim 1, further comprising receiving, by the one or more processors, operational parameter data, and wherein determining the control parameters for the artificial heart comprises determining control parameters to achieve operational parameters of the operational parameter data.

3. The method of claim 1, further comprising monitoring, by the one or more processors, a communication channel with the artificial heart for one or more trigger conditions, and upon detecting a trigger condition, causing the artificial heart to operate in a safety mode at a constant blood flow rate.

4. The method of claim 1, wherein receiving the sensor data comprises receiving one or more of: blood pressure data, blood oxygenation data, body temperature data, or blood glucose level data.

5. The method of claim 4, wherein receiving the sensor data comprises receiving sensor data generated by one or more sensors of the artificial heart and transmitted on a communication channel.

6. The method of claim 4, wherein receiving the sensor data comprises receiving sensor data generated by one or more sensors attached to the body of the patient.

7. The method of claim 1, further comprising:
receiving, by the one or more processors, user input requesting a heart rate boost; and
causing, by the one or more processors, data indicative of the heart rate boost to be transmitted to the artificial heart on a communication channel to cause the artificial heart to adjust the target operational parameters to achieve the heart rate boost.

8. The method of claim 1, wherein:
receiving, by the one or more processors, the user input associated with the patient comprises receiving the user input from a software application operating on a mobile user computing entity.

9. The method of claim 8, wherein:
the mobile user computing entity comprises a mobile phone of the patient; and
the user input is based at least in part on a selection to a graphical user interface (GUI) rendered on a display of the mobile phone.

* * * * *